(12) United States Patent
Hochman

(10) Patent No.: US 7,625,354 B2
(45) Date of Patent: Dec. 1, 2009

(54) HANDPIECE FOR FLUID ADMINISTRATION APPARATUS

(75) Inventor: Mark Hochman, Lake Success, NY (US)

(73) Assignee: Milestone Scientific, Inc., Livingston, NJ (US)

( * ) Notice: Subject to any disclaimer, the term of this patent is extended or adjusted under 35 U.S.C. 154(b) by 620 days.

(21) Appl. No.: 11/271,563

(22) Filed: Nov. 11, 2005

(65) Prior Publication Data

US 2006/0102174 A1 May 18, 2006

Related U.S. Application Data

(60) Continuation-in-part of application No. 10/827,969, filed on Apr. 20, 2004, now Pat. No. 7,449,008, which is a continuation-in-part of application No. 09/766,772, filed on Jan. 22, 2001, now Pat. No. 6,786,885, which is a division of application No. 09/201,464, filed on Nov. 30, 1998, now Pat. No. 6,200,289.

(60) Provisional application No. 60/502,379, filed on Sep. 12, 2003, provisional application No. 60/081,388, filed on Apr. 10, 1998.

(51) Int. Cl.
*A61M 37/00* (2006.01)

(52) U.S. Cl. ............................ 604/131; 604/65; 604/66; 604/67; 604/890.1; 604/118; 604/119; 137/68.11

(58) Field of Classification Search ............. 604/65–67, 604/118, 119, 121, 131, 890.1; 433/27–29, 433/128; 285/1, 2, 3; 251/149
See application file for complete search history.

(56) References Cited

U.S. PATENT DOCUMENTS

| | | | | |
|---|---|---|---|---|
| 1,682,344 A | | 8/1928 | Lesieur | |
| 2,702,547 A | | 2/1955 | Glass | 128/218 |
| 2,852,169 A | * | 9/1958 | Kiffer et al. | 222/396 |
| 3,162,470 A | * | 12/1964 | Owens et al. | 285/86 |
| 3,565,076 A | | 2/1971 | Kadan | 128/278 |

(Continued)

FOREIGN PATENT DOCUMENTS

BR        MU 7502580-9 U        2/1997

OTHER PUBLICATIONS

International Search Report dated May 26, 2006 (2 pgs).

(Continued)

*Primary Examiner*—Nicholas D Lucchesi
*Assistant Examiner*—Scott Medway

(57) ABSTRACT

A handpiece assembly is provided that is adapted for use with a medication infusion system that applies pressure to the handpiece assembly for delivering medication to a body. The handpiece assembly includes a cartridge holder that is configured for disposal of a medication cartridge. A tubing is provided having a first end, which is sealed with the cartridge holder such that the cartridge holder facilitates communication between the tubing and the medication cartridge. A handpiece is sealed with a needle and the second end of the tubing so that the tubing and the needle are in communication. One of the cartridge holder, the tubing, the needle or the handpiece is configured for a selective structural failure at a predetermined pressure threshold applied to the handpiece assembly from the medication infusion system. The cartridge holder may be designed to facilitate aspiration.

16 Claims, 12 Drawing Sheets

U.S. PATENT DOCUMENTS

| | | | |
|---|---|---|---|
| 3,572,319 A | 3/1971 | Bittner et al. | 128/2 |
| 3,623,474 A | 11/1971 | Hellman et al. | 128/2 R |
| 3,976,069 A | 8/1976 | Ong | 128/218 D |
| 4,168,707 A | 9/1979 | Douvas et al. | 128/276 |
| 4,232,697 A * | 11/1980 | Meisenheimer, Jr. | 137/68.15 |
| 4,395,258 A | 7/1983 | Wang et al. | 604/65 |
| 4,403,988 A | 9/1983 | Binard et al. | 604/118 |
| 4,533,346 A | 8/1985 | Cosgrove, Jr. et al. | 604/66 |
| 4,684,367 A * | 8/1987 | Schaffer et al. | 604/140 |
| 4,710,172 A | 12/1987 | Jacklich et al. | 604/118 |
| 4,731,058 A | 3/1988 | Doan | 604/155 |
| 4,747,824 A | 5/1988 | Spinello | 604/51 |
| 4,781,686 A * | 11/1988 | Erickson | 604/118 |
| 4,795,424 A | 1/1989 | Burner | 604/30 |
| 4,800,913 A * | 1/1989 | Nitzberg et al. | 137/68.14 |
| 4,834,705 A | 5/1989 | Vaillancourt | 604/83 |
| 4,921,000 A * | 5/1990 | King et al. | 137/68.14 |
| 4,936,833 A * | 6/1990 | Sams | 604/232 |
| 4,988,336 A | 1/1991 | Kohn | 604/67 |
| 5,080,653 A | 1/1992 | Voss et al. | 604/152 |
| 5,147,329 A | 9/1992 | Brannon | 604/231 |
| 5,169,388 A * | 12/1992 | McPhee | 604/90 |
| 5,180,371 A | 1/1993 | Spinello | 604/118 |
| 5,295,967 A | 3/1994 | Rondelet et al. | 604/154 |
| 5,310,161 A * | 5/1994 | Bryce | 251/149.6 |
| 5,352,195 A | 10/1994 | McEwen | 604/66 |
| 5,383,858 A * | 1/1995 | Reilly et al. | 604/152 |
| 5,450,973 A | 9/1995 | Ellis et al. | 215/252 |
| 5,515,851 A * | 5/1996 | Goldstein | 600/431 |
| 5,527,307 A * | 6/1996 | Srisathapat et al. | 604/892.1 |
| 5,681,285 A | 10/1997 | Ford et al. | 604/151 |
| 5,690,618 A | 11/1997 | Smith et al. | 604/232 |
| 5,743,879 A * | 4/1998 | Kriesel | 604/132 |
| 5,830,180 A * | 11/1998 | Chandler et al. | 604/65 |
| 5,840,071 A * | 11/1998 | Kriesel et al. | 604/132 |
| 6,002,337 A | 12/1999 | Palfey et al. | 340/606 |
| D423,665 S | 4/2000 | Herbst et al. | D24/111 |
| 6,113,574 A | 9/2000 | Spinello | |
| 6,132,414 A | 10/2000 | Herbst et al. | 604/403 |
| 6,152,734 A | 11/2000 | Herbst et al. | 433/82 |
| 6,200,289 B1 | 3/2001 | Hochman et al. | 604/67 |
| 6,296,623 B2 | 10/2001 | Spinello | |
| 6,520,928 B1 | 2/2003 | Junior | 604/30 |
| 6,652,482 B2 | 11/2003 | Hochman | 604/65 |
| 6,786,885 B2 | 9/2004 | Hochman et al. | 604/67 |
| 6,887,216 B2 | 5/2005 | Hochman et al. | 604/67 |
| 6,945,954 B2 | 9/2005 | Hochman et al. | 604/67 |
| 6,984,204 B2 * | 1/2006 | Akiba | 600/158 |
| 2002/0077588 A1 | 6/2002 | Schneider et al. | 604/82 |
| 2002/0183701 A1 | 12/2002 | Hochman et al. | 604/264 |
| 2004/0116869 A1 | 6/2004 | Heinz et al. | 604/181 |
| 2004/0122367 A1 | 6/2004 | Sculati | 604/140 |
| 2004/0171985 A1 | 9/2004 | Schubert et al. | 604/93.01 |
| 2005/0004514 A1 | 1/2005 | Hochman | 604/67 |

OTHER PUBLICATIONS

"The periodontal ligament (PDL) injection: An alternative to inferior alveolar nerve block" by S. F. Malamed, oral surgery . . . vol. 53, No. 2, Feb. 1982.

"Intraligamentary anaesthesia" by J. G. Meechan, J. Dent. 1992; 20: 325-332.

* cited by examiner

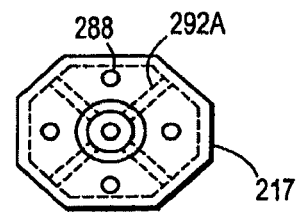
FIG. 12
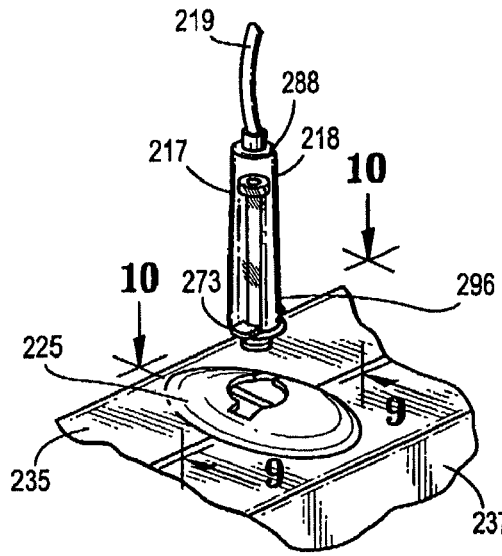
FIG. 8
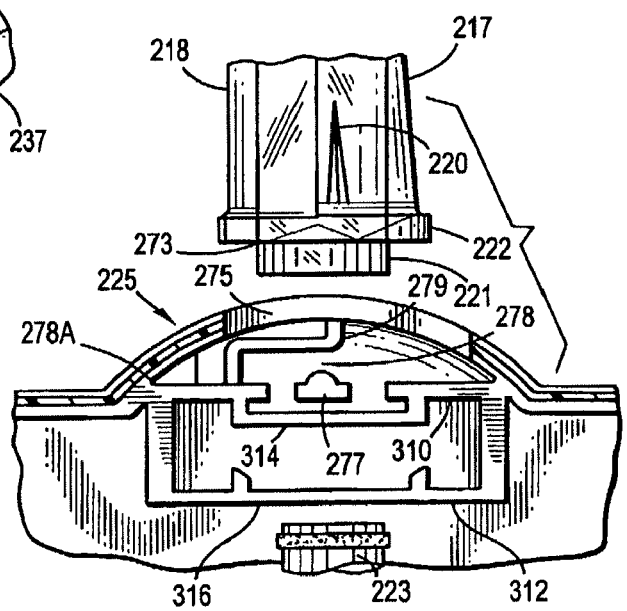
FIG. 9
FIG. 10

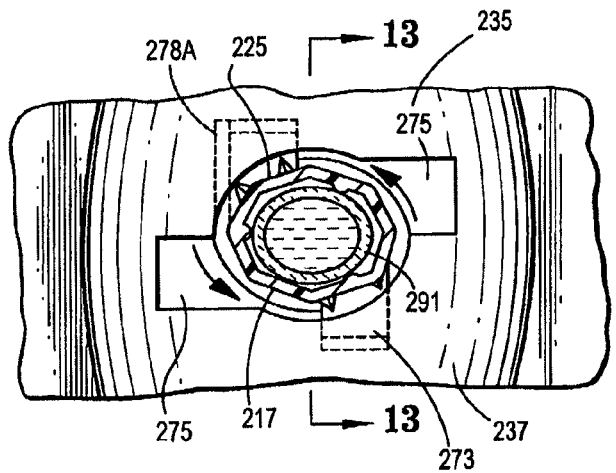
FIG. 11
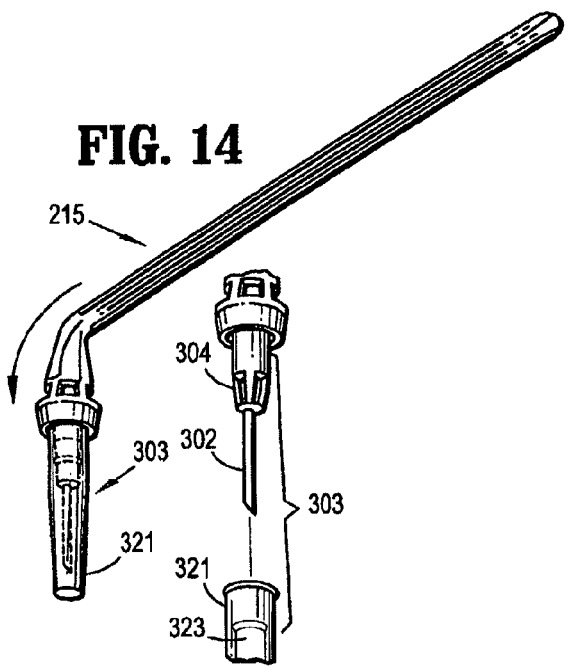
FIG. 14
FIG. 15
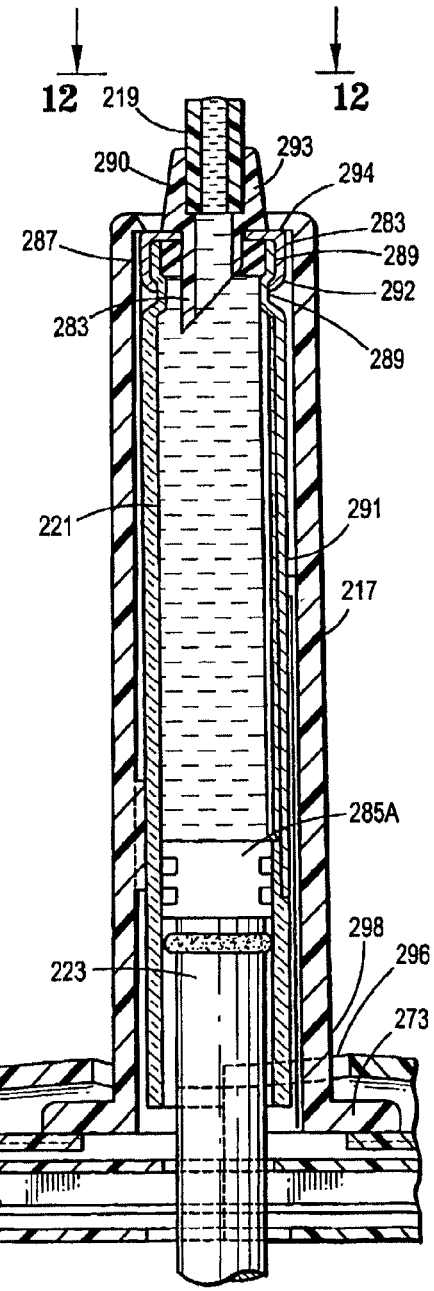
FIG. 13

HANDPIECE FOR FLUID ADMINISTRATION APPARATUS

CROSS-REFERENCE TO RELATED APPLICATIONS

This patent application is a continuation-in-part of U.S. Utility patent application Ser. No. 10/827,969, filed in the U.S. Patent and Trademark Office on Apr. 20, 2004, now U.S. Pat. No. 7,449,008, by Hochman, which is a continuation-in-part of U.S. Utility patent application Ser. No. 09/766,772, filed Jan. 22, 2001, now U.S. Pat. No. 6,786,885, which is a division of U.S. patent application Ser. No. 09/201,464, filed Nov. 30, 1998, now U.S. Pat. No. 6,200,289; application Ser. No. 10/827,969 claims the benefit of U.S. Provisional Patent Application Ser. No. 60/502,379, filed Sep. 12, 2003; application Ser. No. 09/201,464 claims the benefit of U.S. Provisional Patent Application Ser. No. 60/081,388, filed on Apr. 10, 1998, the entire contents of each of these disclosures being hereby incorporated by reference herein.

BACKGROUND

1. Technical Field

The present disclosure relates generally to the administration of fluids to a body, particularly to medication infusion systems for subcutaneous injection/aspiration. More specifically, the present disclosure is directed to handpieces for such medication infusion systems that facilitate operability over a range of pressure for infusing medication safely and painlessly during a medical and/or dental procedure.

2. Description of the Related Art

Infusion pump devices and related systems are well known in the medical arts for use in the administration of medication to a patient. The administration of medication has been described in the art as administration to a patient through infusion tubing and an associated catheter, needle cannula, or the like, to introduce the medication intravenously. Some of these systems can determine infusion line occlusion. Line occlusions may cause the pressure in a syringe of the system to increase. Various systems are available to identify a predetermined threshold or to monitor pressure to determine selected ranges of occlusion pressures to insure patient safety. See, for example, U.S. Pat. Nos. 5,295,967; 4,731,058; and 5,080,653, which disclose systems (with syringe pumps or the like) intended for use of intravenous drug delivery and more specifically for monitoring occlusion during infusion. However, these systems do not provide drug delivery or aspiration subcutaneously via a hypodermic needle.

Accurately positioning a hollow-bore needle within tissues to deliver medication within tissue structures has long been a challenge in both medicine and dentistry. The inability to accurately position a hollow-bore needle within specific tissues (e.g., soft-tissues) or organs can lead to a failed medical objective. Locating pathologic tissue types (e.g., neoplasia, tumors, cysts and the like) is relevant to aspiration of these tissues as well as the infusion of therapeutic medications to treat these local lesions of the body. Hence, locating a specific anatomical site has been previously assisted by using ionizing radiation, ultrasound, MRI, electrical-stimulators and other invasive diagnostic devices that require secondary techniques to be employed to assist the practitioner in determining the accuracy of the placement of a needle within tissue.

Pain, tissue damage and post-op complications have long been tolerated as negative side effects from the use of existing hypodermic medication delivery injection systems. The pain and tissue damage are a result of uncontrolled flow rate in conjunction with excessive pressures created during the administration of medication solutions within the tissue spaces. Subjective pain response of a patient has been demonstrated to be minimized at specific flow rates during the administration of a medication. Also, it is known that particular pressures, such as those that are excessive without occlusion, for a specific tissue type can cause damage.

Various devices have been disclosed in an attempt to overcome the above referenced complications and related issues. See, for example, U.S. Pat. Nos. 4,747,824; 5,180,371. These devices typically include a handpiece for administering medication from a vial, cartridge, etc. to a patient. The handpiece assembly may include various components such as, for example, conduits, needle assembly, cartridge holder, etc. These handpiece assemblies can suffer from a variety of drawbacks and disadvantages. For example, many of these disposable handpiece assemblies are not suitable for a specific high pressure range. Under high pressure conditions the components of the handpiece assembly are susceptible to distortion, deformation of shape, fracture and leakage resulting in failure to achieve the desired clinical effect.

Further, handpieces that require a practitioner to affix a needle of the assembly suffer from the risk of improper installation, which may result in leakage during use. Improper connection of tubing of the handpiece assembly, such as connection to a cartridge carrier, can lead to leakage at the corresponding interface, particularly at high pressures. Practitioner assembly can also result in an inadequate tightening and sealing of components. Minor variations in manufacturing tolerances of components of the handpiece assembly, in particular needle hubs may result in discrepancies between components such that upon assembly, leakage may occur.

Moreover, microbore tubing used with such handpiece assemblies can deform under pressure resulting in an internal ballooning. This ballooning of tubing results in ineffective infusion/aspiration as solution becomes retained within tubing thereby preventing administration of fluid. In particular, microbore tubing is susceptible to distortion under specific pressures. This specific pressure range can lead to deformation of tubing in which tubing absorbs the medication solution within the physical length of tubing resulting in ballooning of the micro-tubing. When this occurs the solution is retained within the micro-tubing and does not reach the intended tissue site, disadvantageously leading to failure.

Therefore, it would be desirable to overcome the disadvantages and drawbacks of the prior art with a handpiece for a medication infusion system that facilitates operability over a range of pressure for infusing medication safely and painlessly during a medical and/or dental procedure. Desirably, the handpiece of the medication infusion system is a disposable handpiece assembly including a needle, tubing and cartridge holder, which utilize a sealing bond to ensure a lack of fluid leakage or distortion of the system components for a specified range of pressures. Most desirably, the handpiece assembly of the medication infusion system is configured for operability in a range of 200 pounds per square inch (psi) to 650 psi, to achieve the principles of the present disclosure. It is contemplated that the handpiece assembly of the medication infusion system and its constituent parts are easily and efficiently manufactured and assembled.

SUMMARY

Accordingly, a handpiece for a medication infusion system is provided that facilitates operability over a range of pressure for infusing medication safely and painlessly during a medical and/or dental procedure for overcoming the disadvantages and drawbacks of the prior art. Desirably, the handpiece of the medication infusion system is a disposable handpiece assembly including a handpiece, needle, tubing and cartridge holder, which utilize a sealing bond to ensure a lack of fluid leakage or distortion of the system components for a specified range of pressure. Most desirably, the handpiece assembly of the medication infusion system is configured for operability in a range of 200 psi to 650 psi to achieve the principles of the present disclosure. The handpiece assembly of the medication infusion system is easily and efficiently manufactured and assembled. The present disclosure resolves related disadvantages and drawbacks experienced in the art.

The present disclosure provides a handpiece assembly that can be employed with an infusion/aspiration system that includes a drive mechanism, which causes a therapeutic fluid to flow from a cartridge supported by a cartridge holder, a tube and a handle with an injection needle. The drive mechanism is connected to an electric motor and a sensor positioned at the motor output that measures the force applied by the motor to the drive mechanism. This force is then used to determine an internal characteristic such as a force or internal pressure generated during the injection process. This characteristic is then used as a control parameter by a microprocessor or controller, which generates corresponding commands to the drive mechanism. In a particularly advantageous embodiment, the characteristic is used to calculate an exit pressure at which fluid is expelled by the device through an elongated tube. The electric motor is then operated in such a manner that the exit pressure is maintained at a predetermined level to insure that a patient does not suffer pain and/or tissue damage.

In one particular embodiment, in accordance with the present disclosure, a handpiece assembly is provided that is adapted for use with a medication infusion system that applies pressure, in a range of 200 to 650 psi, to the handpiece assembly for delivering medication to a body. The handpiece assembly includes a cartridge holder that is configured for disposal of a medication cartridge. The cartridge holder is connected with the medication infusion system. A tubing is provided having a first end. The first end is sealed with the cartridge holder such that the cartridge holder facilitates communication between the tubing and the medication cartridge. A handpiece is sealed with a needle and the second end of the tubing so that the tubing and the needle are in communication. One of the cartridge holder, the tubing, the needle or the handpiece is configured for a selective structural failure at a predetermined pressure threshold applied to the handpiece assembly from the medication infusion system. This design of the present disclosure advantageously prevents leakage outside of the system.

Alternately, the needle may include a needle sleeve configured to bond with the handpiece. The needle may be fixedly sealed with the handpiece in a configuration that is impermeable to leakage. The tubing may be fixedly sealed with the handpiece in a configuration that is impermeable to leakage. The tubing may be fixedly sealed with the cartridge holder in a configuration that is impermeable to leakage. The structural failure may include physical deformation, dimensional changes, fracture, elongation, stretching or leakage. The predetermined pressure threshold may be in a range of 450 to 650 psi. Alternatively, the predetermined pressure threshold is 550 psi.

In an alternate embodiment, the cartridge holder includes one or more radially projecting wings configured for engagement with a receptacle of the medication infusion system. The one or more wings of the cartridge holder can be configured for selective structural failure at the predetermined pressure threshold. Alternatively, the cartridge holder includes a plurality of lateral openings such that the openings facilitate selective structural failure of the cartridge holder at the predetermined pressure threshold. The lateral openings may define windows in sidewalls of the cartridge holder. The cartridge holder may include a relatively thin-walled portion such that the thin-walled portion facilitates selective structural failure of the cartridge holder at the predetermined pressure threshold.

In an alternate embodiment, the cartridge holder may also be designed to facilitate the creation of a vacuum for bodily fluid/blood aspiration during use. For example, during the process of injecting drugs or fluids into bodily tissues, it may be advantageous to determine if the injection is being performed within specific tissues to avoid the direct placement of a drug into a blood vessel, e.g., artery or vein. As is known, the technique of creating a vacuum or an aspiration confirms the placement of the needle within a vessel. If blood or fluid is "sucked back" or aspirated into the system, this confirms the placement of a needle within a vessel. The practitioner then repositions the needle if the intention was not be within a vessel or remain in such a position if the operator did have the objective of placing drugs or fluids within the vessel. The cartridge holder of the present disclosure can also facilitate aspiration with the following design features.

Accordingly, the cartridge holder may include a spike oriented to puncture a rubber diaphragm or the like of the medication cartridge upon placement of the cartridge within the cartridge holder. The cartridge holder is designed to be of a greater physical length relative to the cartridge. This configuration facilitates movement of the cartridge relative to the cartridge holder and the spike. As the cartridge is withdrawn from the cartridge holder and the spike by physical movement, a vacuum is created within the cartridge. This vacuum created by the movement of the cartridge, relative to the cartridge holder and the spike produces a vacuum or aspiration effect within the handpiece during use.

Thus, the medication infusion system of the present disclosure can be configured to aspirate fluid from the body during movement of the cartridge away from the spike. It is contemplated that the cartridge holder may contain the entire cartridge during use. The action of withdrawing the cartridge, whereby the relative movement of the cartridge to the cartridge holder along the spike produces the vacuum.

In another alternate embodiment, the handpiece assembly includes a microbore tubing having a first end and a second end. The first end is permanently bonded with the cartridge holder such that the cartridge holder facilitates communication between the tubing and the medication cartridge. The handpiece is permanently bonded with the needle assembly and the second end of the tubing such that the tubing and the needle assembly are in communication. The cartridge holder is configured for a selective structural failure at a predetermined pressure threshold, in the range of 450 to 650 psi, as applied to the hand piece assembly from the medication infusion system.

In another alternate embodiment, a medication infusion system is provided that includes a drive unit having a receptacle and is configured to apply pressure in a range of 200 psi to 650 psi, to a hand piece assembly for delivering medication to a body. A cartridge holder is configured for disposal of a medication cartridge. The cartridge holder is connected with the receptacle of the medication infusion system. Microbore tubing is provided having a first end and a second end. The first end is fixedly sealed with the cartridge holder such that the cartridge holder facilitates communication between the tubing and the medication cartridge. A handpiece is fixedly sealed with a needle assembly and the second end of the tubing such that the tubing and the needle assembly are in communication. The cartridge holder is configured for a selective structural failure at a predetermined pressure threshold, in the range of 450 to 550 psi, as applied to the handpiece assembly from the medication infusion system.

A sensor is coupled to the drive unit for sensing an internal parameter indicative of the pressure being applied by the drive unit and internal resistances within the medication infusion system. A controller is coupled to the sensor and the drive unit. The controller includes a calculator for calculating an exit pressure of the medication at the needle assembly. The controller generates commands to insure the exit pressure does not exceed a predetermined level.

The handpiece can be bonded in a sealing configuration at a luer lock needle to handpiece interface. Such a handpiece/needle attachment avoids the requirement that the components of the system mesh with precise accuracy to create the impenetrable barrier to leakage. Such a sealing configuration may be employed at the interface of the tubing and the handpiece element. Further, the sealing configuration may also be employed at the interface of the tubing and the cartridge holder. This bonding can be achieved via various methodologies, such as, for example, adhesive, sonic bonding/welding, resin bonding agents, chemical bonding agents, etc. It is contemplated that the sealing configuration is designed for a specific pressure range, such as, for example, of 200 psi to 650 psi.

It is envisioned that the tubing selected can be of varying lengths of 6 inches to 80 inches. It is further envisioned that such tubing is configured so that minimal distortion or deformation of shape occurs at a pressure range of 200 psi to 650 psi.

In an alternate embodiment, the cartridge holder is designed to physically deform to a sufficient degree to cause failure of the cartridge holder, such as, for example, separation, fracture, elongation, stretching, etc. at a specific pressure range prior to failure of the remaining components of the handpiece assembly. This configuration advantageously ensures that the other components of the system will not fail and result in leakage of medication solution into the patient's tissues. Failure of the cartridge holder prior to other elements, i.e., microtubing, needle, handpiece and the sealing bonded interfaces to their connection prevents leakage. This is due, at least in part, to the physical failure of the cartridge holder as the spike of the cartridge holder is maintained within the cartridge and failure of the system does not produce an opening along the entire system for medication to leak outside of the sealed system created between the handpiece system and the cartridge. The system is designed with an intentional weak point at the cartridge holder to ensure that failure results in breakage without leakage of medications. It is contemplated that the cartridge holder can be designed to fail at the base of its wings. It is preferable that the cartridge holder fails at a pressure of 525 psi although other pressures are contemplated.

Alternatively, the top of a cartridge holder may have a plurality of openings. The openings allow a weakening of the structure so that failure will result in the separation of the cartridge holder at a point in which the cartridge stays embedded with the spike that penetrates the anesthetic cartridge rubber diaphragm. Accordingly, this structural failure point prevents leakage of medication or other gases, fluids, etc., outside of the sealed system created by the cartridge and the handpiece system described.

This advantageous handpiece configuration can be bonded in a sealed configuration to withstand pressures between 200 psi to 650 psi. The tubing will not deform or distort between 200 psi to 650 psi. This configuration also eliminates operator error in affixing the needle to the handpiece. The handpiece assembly is designed so that failure will occur at a specific component of the handpiece assembly prior to failure of the remaining components of the handpiece of the assembly. This configuration avoids medication or other gases, fluids, etc., from leaking into patient's tissues or possibly spraying out of a leakage point that can contaminate the practitioner or cause harm to the skin or eyes. Preferably, the handpiece assembly includes a 30 gauge ½ inch Luer Lock needle affixed to the assembly. It is contemplated that other needle sizes and lengths may be used.

BRIEF DESCRIPTION OF THE DRAWING

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, as set forth below.

FIG. 8 is a perspective view illustrating the placement of an anesthetic cartridge and cartridge holder of the system shown in FIG. 7;

FIG. 9 is a side view, in partial cross-section, showing the cartridge holder disposed above a drive unit receptacle of the system shown in FIG. 7;

FIG. 10 is a top plan view, in partial cross-section, illustrating engagement of the cartridge holder in the receptacle of the system shown in FIG. 7;

FIG. 11 is a top plan view, in partial cross-section, similar to FIG. 10;

FIG. 12 is a top view of a forward end of the cartridge holder, taken along line 12-12 in FIG. 13;

FIG. 13 is a cross-sectional view taken along line 13-13 of FIG. 11;

FIG. 14 is a perspective view of an alternate embodiment of the handpiece unit of the system shown in FIG. 7;

FIG. 15 is a perspective view of the needle assembly of the system shown in FIG. 7;

DETAILED DESCRIPTION OF EXEMPLARY EMBODIMENTS

The exemplary embodiments of the present disclosure relate generally to the administration of fluids to a body, particularly relating to medication infusion systems for subcutaneous injection/aspiration. More particularly, the present disclosure is directed to a handpiece assembly for such medication infusion systems that facilitate operability over a range of pressure for infusing medication safely and painlessly during a medical and/or dental procedure. It is envisioned that the present disclosure may be employed with a range of applications for administration of fluids, gases, etc. to a body including portable, care facility, in-home and in-office. It is further envisioned that the present disclosure may be applicable with various dental and medical applications, including diagnostic, treatment and surgical. The device and techniques described herein are applicable to human and other animal tissues.

Figure 1:
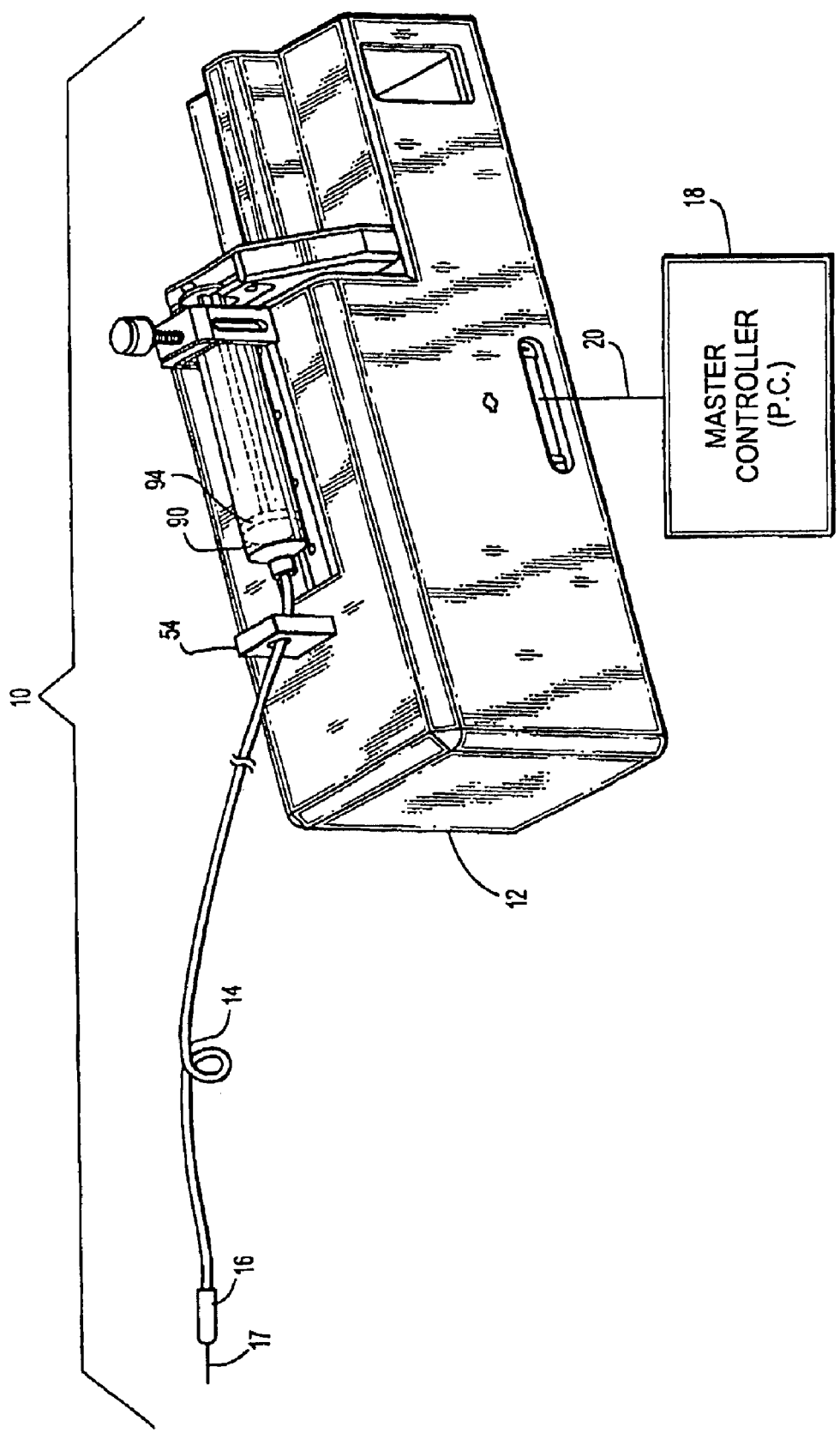
FIG. 1 is a perspective view of a mediation infusion system in accordance with the principles of the present disclosure.
Figure 2:
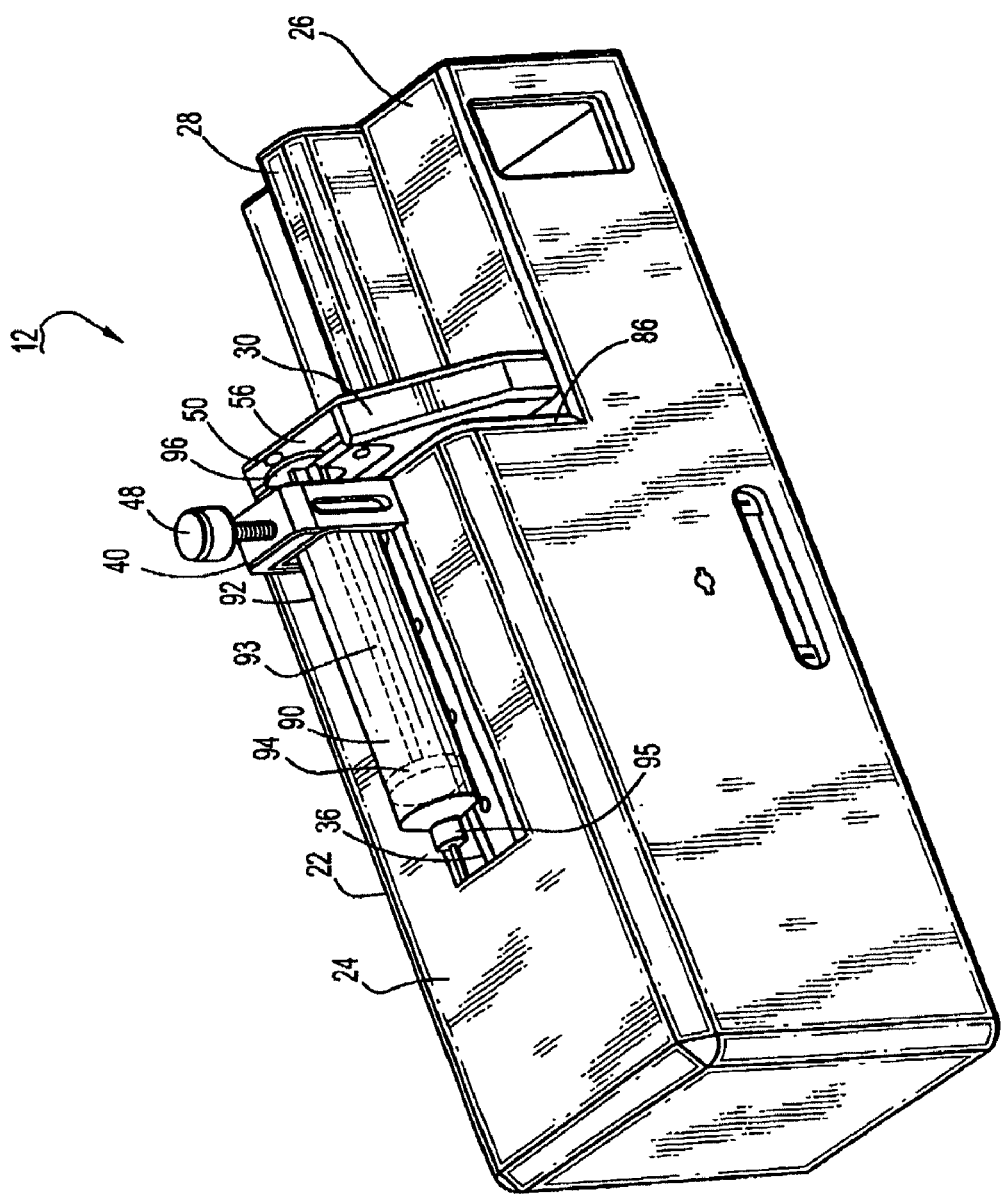
FIG. 2 is a perspective view of a drive mechanism of the medication infusion system shown in FIG. 1.

The following discussion includes a description of a medication infusion system in connection with an exemplary method of operating the medication infusion system in accordance with the principles of the present disclosure. Alternate embodiments are also disclosed. Reference will now be made in detail to the exemplary embodiments of the present disclosure, which are illustrated in the accompanying figures. Turning now to FIGS. 1 and 2, there is illustrated a medical infusion system, such as, for example, a drug delivery system 10, in accordance with the principles of the present disclosure.

The components of drug delivery system 10 are fabricated from materials suitable for dental and/or medical applications, such as, for example, polymerics or metals, depending on the particular application and/or preference. Semi-rigid and rigid polymerics are contemplated for fabrication, as well as resilient materials, such as molded medical grade polyurethane, etc. One skilled in the art, however, will realize that other materials and fabrication methods suitable for assembly and manufacture, in accordance with the present disclosure, also would be appropriate.

Detailed embodiments of the present disclosure are disclosed herein, however, it is to be understood that the described embodiments are merely exemplary of the disclosure, which may be embodied in various forms. Therefore, specific functional details disclosed herein are not to be interpreted as limiting, but merely as a basis for the claims and as a representative basis for teaching one skilled in the art to variously employ the present disclosure in virtually any appropriately detailed embodiment.

Figure 4:
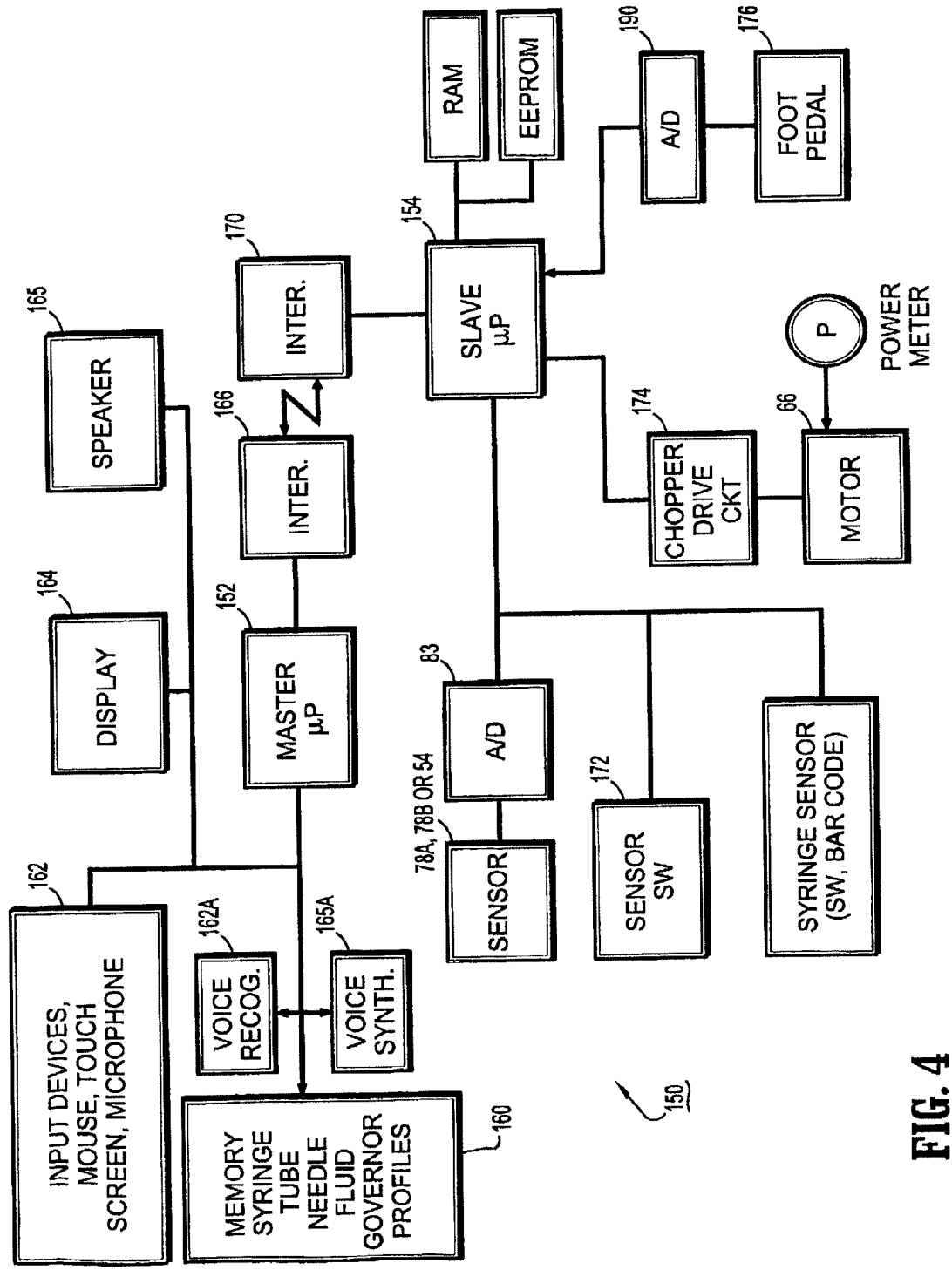
FIG. 4 is a block diagram of an electronic controller of the medication infusion system shown in FIG. 1.

Drug delivery system 10 is configured for the delivery of drugs such as an anesthetic, under pressure into a body, such as, for example, patient tissues and animal tissues. Due to a variety of factors, injected fluid disperses through a tissue at different rates, causing the fluid exit pressure to vary. Such exit pressure (or an internal pressure related to the exit pressure) is indicative of, and may be used to identify several types of tissues. An electronic controller 150 for the system is shown in FIG. 4.

Drug delivery system 10 includes drive mechanism 12, a delivery tube 14 and a handle 16 terminating with a needle 17. A syringe 90 (or other fluid storage device) is mounted on drive mechanism 12 with one end of tube 14 being coupled to syringe 90. Drive mechanism 12 operates a plunger 94 to selectively eject fluid out through tube 14, handle 16, and needle 17 or alternatively to draw fluid in. Drive mechanism 12 is associated with an external controller for selecting various operational parameters discussed in more detail below. This external controller may be provided on the housing of drive mechanism 12 or may be provided as a separate control unit 18 coupled to drive mechanism 12 by a cable 20. Control unit 18 may be, for instance, a personal computer or laptop computer. Alternatively, control unit 18 may be internal.

As shown in FIG. 2, drive mechanism 12 includes a housing 22 with a top surface 24 and an intermediate surface 26 disposed below top surface 24. Surface 26 includes a rail 28 extending along the longitudinal axis of housing 22. A platform 30 is disposed on rail 28 and is disposed for reciprocal movement back and forth in parallel with the longitudinal axis, as described in more detail below. Top surface 24 has a clamp 40 with a generally C-shaped body. A screw 48 extends through a threaded hole (not shown) in the body of clamp 40. Platform 30 has a slot 56.

Figure 3:
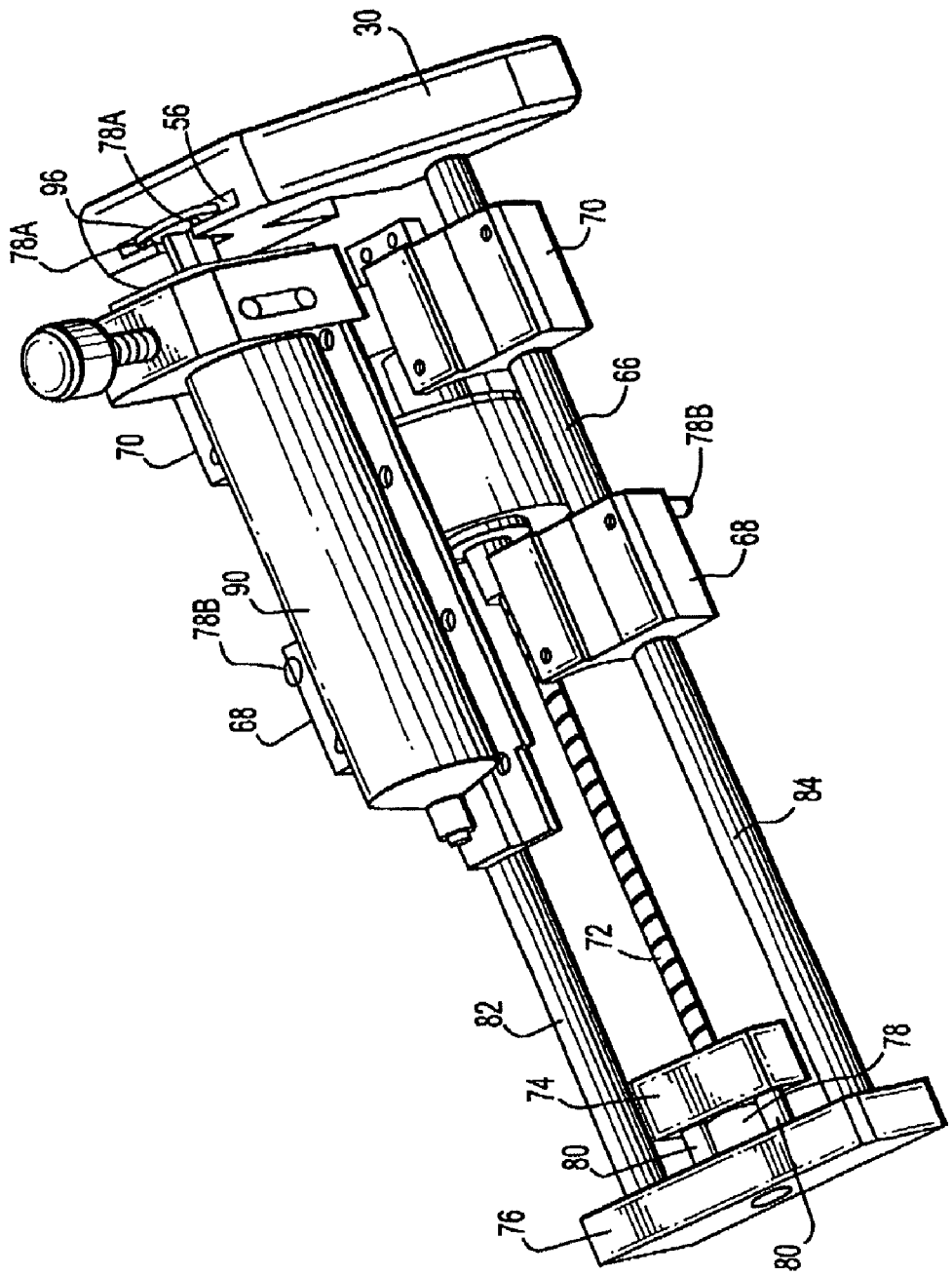
FIG. 3 is a perspective view of the inner components of the drive mechanism shown in FIG. 2.

Housing 22 includes a motor 66 disposed therein, as shown in FIG. 3. Motor 66 has a threaded worm screw 72. Worm screw 72 is arranged so that as motor 66 is activated, worm screw 72 moves in one direction or another, dependent on its direction of rotation, in parallel with the longitudinal axis of housing 22. One end of worm screw 72 is non-rotatably attached to a pad 74, coupled to a platform 76. Short rods 80 couple pads 74 to platform 76, to prevent the transmission of rotational forces generated by motor 66 to platform 76.

Columns or rods 82, 84 extend between platforms 30 and 76 for recurrent thereof. Rods 82, 84 are slidably supported by two pairs of bushings 68, 70 on housing 22. Except for these bushings, platforms 76 and 30 are floating respectively inside and outside housing 22. Rods 82, 84 extend through wall 86 (FIG. 2) extending between surfaces 24 and 26 via holes (not shown). Rail 28 is hollow and aligned with worm screw 72 to allow worm screw 72 to move longitudinally along its axis through housing 22.

Syringe 90 has a barrel 92 on surface 24. Barrel 92 has a finger tab resting in a slot formed on surface 24. The finger tab and the slot have been omitted from the drawings for clarity. Syringe 90 also includes a plunger 94 reciprocated within barrel 92 by a shaft 93. Shaft 93 terminates in a finger pad 96 resting in slot 56 of platform 30. Syringe 90 is secured to housing 22 by clamp 40 and screw 48. Syringe 90 terminates with a luer lock 95 used to connect syringe 90 to tube 14.

When motor 66 is activated it forces worm screw 72 to move in one direction or another. Worm screw 72 in turn forces platforms 30, 76 and rods 82 and 84 to move concurrently, thereby forcing plunger 94 to reciprocate within barrel 92. Rods 82, 84 move in and out of housing 22. It is contemplated that drive mechanism 12 is adapted to receive and operate with syringes of various diameters and lengths. It is further contemplated that delivery tube 14, handle 16 and needle 17 may be variously sized. Alternatively, as shown in FIG. 3, system 10 includes a pair of pressure sensors 78A disposed between finger pad 96 and the walls of slot 56. Sensors 78A are arranged to measure the force applied between platform 30 and finger pad 96. In another embodiment, sensors 78B are provided between bushings 68 and the sidewalls of housing 22. In this manner, sensors 78B can measure the force (or strain) resultant from the force applied by motor 66 on syringe plunger 94. Alternatively, a similar load cell may be placed between pad 96 and housing 22. Sensors may be load cells, for instance a Model S400 load cell made by the SMD, Inc. of Meridien, Conn. may be used.

In yet another embodiment, as shown in FIG. 1, tubing 14 passes through a hole in a size gauge 54. When tubing 14 is pressurized, it expands, and therefore, the size of tubing 14 is indicative of the pressure applied by plunger 94. Size gauge 54 monitors the size (e.g. cross-sectional dimension, or diameter) of tubing 14 and provides this parameter to master controller 18. For example, gauge 54 may include one or more LEDs and an array of light sensors with tubing 14 disposed therebetween. The size of tubing 14 is determined by the number and/or position of the light sensors occluded by tubing 14.

Figure 5:
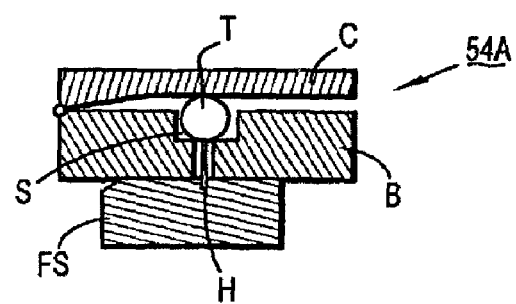
FIG. 5 is an alternate embodiment of a pressure gauge of the medication infusion system shown in FIG. 1.

In an alternate embodiment of gauge 54, as shown in FIG. 5, a cross-section of gauge 54A includes a base B with a slot S holding tubing T. A hinged cover C holds tubing T in place. A force sensor FS is inserted through a hole H and rests against tubing T. As tubing T expands and contracts due to pressure changes, it applies a force on force sensor FS. Experimental data shows that gauge 54A has a substantially linear output for calibration of various pressures.

Figure 6:
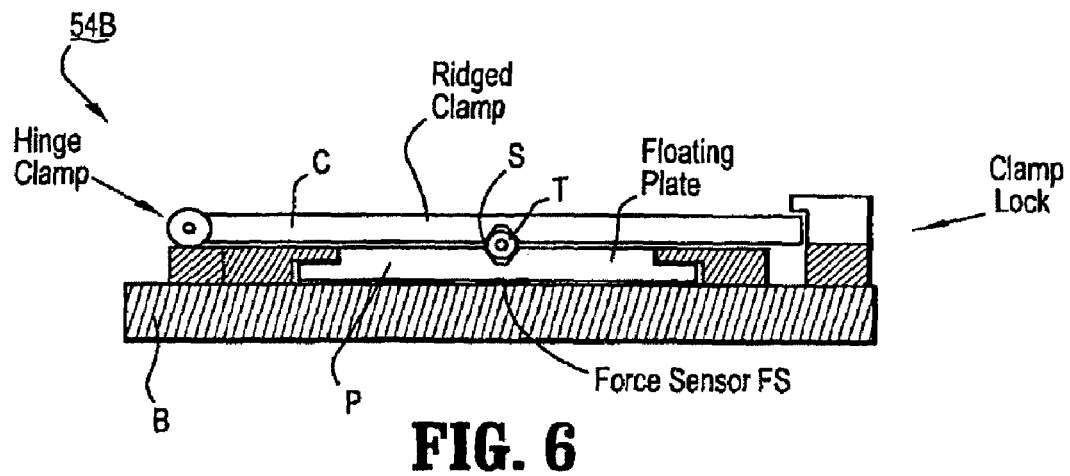
FIG. 6 is another embodiment of the pressure gauge shown in FIG. 5.

In another alternate embodiment, as shown in FIG. 6, a gauge 54B, similar to those described, has a groove in a cover C and tube T is resting on a floating platform P disposed above force sensor FS. The force generated by the pressure within tube T is transmitted by floating platform P to force sensor FS.

Referring to FIG. 4, a block diagram of electronic controller 150 for an injection application is shown illustrating two microprocessors: a master microprocessor 152 and a slave microprocessor 154. Slave microprocessor 154 derives the signals that drive motor 66 and collect information regarding the position of platforms 30, 76. Master microprocessor 152 collects information regarding the remaining components of system 10, including syringe 90, and its contents, tube 14, handle 16, etc., and generates control signals for slave microprocessor 154 necessary for operating motor 66 to deliver the contents of syringe 90.

Slave microprocessor 154 and its associated circuitry are disposed within housing 22. Master microprocessor 152 is incorporated into control unit 18, which is coupled to housing 22 through cable 20, as shown in FIG. 1. Microprocessor 152 is associated with a memory 160, input devices 162, display devices 164 and an interface 166.

Memory 160 is used to store programming and data for master microprocessor 152. Memory 160 stores six or more data banks, each of the data banks being dedicated to the following information: (a) syringes; (b) tubing; c) needles; (d) fluids; (e) governor parameters; and (f) profiles consisting of a plurality of parameters for a particular procedure to be performed. Each of these parameters is used to determine the control signals generated for slave microprocessor 154. Each of these data banks contains the appropriate parameters for various commercially available products, or alternatively, parameter data derived using a specific algorithm. Information regarding the various elements for a particular configuration is entered through input devices 162 and is confirmed on display device 164. These input devices may include a keyboard, a touch screen, a mouse, as well as a microphone. If a microphone is included, voice commands are interpreted by a voice recognition circuit 162A.

Display device 164 provides an indication, as well as instructions, on the operation of system 10. The commands for the operation of motor 66 are generated by master microprocessor 152 and transmitted to an interface 166. Microprocessor 152 has a speaker 165 that provides various oral messages (generated by a voice synthesized circuit 165A) to provide instructions to the practitioner and to provide other information about the current status of system 10 and its components. Speaker 165 may also provide auditory sounds that relate to the pressure that is generated by motor 66. These auditory sounds may also provide instructions to the practitioner and provide information about the current status of system 10 and its components. The slave microprocessor 154 receives these commands through cable 20. Slave microprocessor 154 is associated with one or more position sensors 172 and a chopper drive circuit 174. Slave microprocessor 154 is associated with a foot pedal 176. A pressure sensor (not shown) is part of foot pedal 176 to provide information about the pressure to slave microprocessor 154 via a corresponding A/D converter 190.

Drug delivery system 10 delivers an anesthetic under pressure into a patient's tissues. See, for example, the operations and systems disclosed in U.S. Pat. No. 6,200,289. It is envisioned that system 10 may be employed for a biopsy, for instance to perform a spinal tap, or other similar anaerobic procedures. It is contemplated that the same parameters can be used for this process, with some minor modifications. For instance, instead of defining an exit pressure, the practitioner can define an entry pressure.

System 10 disperses a fluid medication from syringe 90 such that syringe 90 is preloaded with the fluid medication either by the manufacturer, or may be filled at the site by the practitioner or an assistant prior to the start of any operation. In many procedures, however, it is more desirable to provide the fluid medication to be dispensed in a cartridge. See, for example, U.S. Pat. No. 6,152,734, the contents of which being hereby incorporated by reference herein. Thus, in an alternate embodiment of system 10, an injection device is described below that includes a housing with a motor driven shaft. On top of the housing, a receptacle is provided for accepting a cartridge holder. The cartridge holder receives a cartridge with an anesthetic. The holder has a top wall connected to the proximal end of tubing. The distal end of tubing is used to deliver an anesthetic through its distal end.

Figure 7:
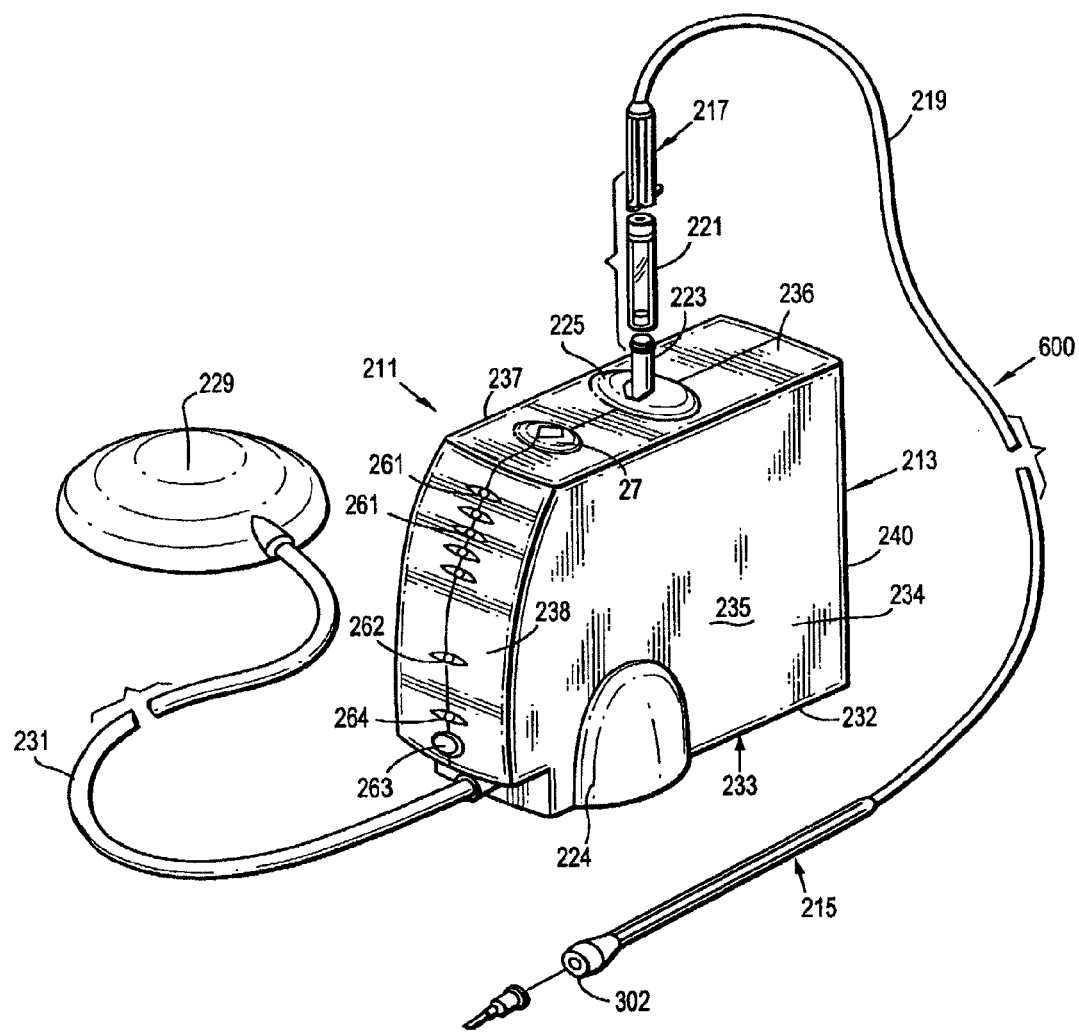
FIG. 7 is a perspective view of a dental anesthetic injection delivery system in accordance with the principles of the present disclosure.

Referring to FIG. 7, an alternate embodiment of system 10 is shown. A medication infusion system, such as, for example, a dental anesthetic injection delivery system 211, similar to that described above with regard to FIGS. 1-4, in accordance with the principles of the present disclosure. System 211 includes a drive unit 213, similar to drive mechanism 12 described above, a foot pedal 229, similar to foot pedal 176 described above, which is connected to drive unit 213 by an air hose 231, an anesthetic cartridge holder 217 for selectively retaining a cartridge 221 of a desired anesthetic, and a handpiece unit 215, which is connected to anesthetic cartridge holder 217 by a predetermined length of microtubing 219. System 211 includes a control circuit, similar to controller 150 described above.

Drive unit 213 has a substantially rectangular housing 233 having a base 232, sides 234, top 236, front portion 238 and rear portion 240. Housing 233 is defined by two mating and engageable halves 235 and 237. Housing 233 includes a pair of lateral hubs 224 disposed on sides 234 of each housing half 235 and 237 along base 232 to stabilize drive unit 213 as it stands on a supporting surface.

Housing 233 of drive unit 213 includes a power switch (not shown) along back portion 240 and a reset 263 or aspirate with other controls, which can be selectively pressed to operate system 211. Front portion 238 of housing 233 includes a series of cartridge volume indicator lights 261, a power indicator light 262, and an aspirate indicator light 264. Preferably, lights 261, 262, 264 are LED's.

Referring to FIGS. 8-13, cartridge holder 217 holds anesthetic cartridge 221 in proper engaged position in drive unit 213 to enable controlled dispensing of anesthetic solution to handpiece unit 215 for delivery therefrom. Cartridge holder 217 has an elongated plastic transparent cylindrical tube 271 having a forward end 294 and a rear end 296. Cartridge holder 217 has a greater physical length relative to cartridge 221. Forward end 294 includes an outwardly projecting delivery sleeve 293 and an inwardly projecting protrusion or spike 283, both of which serve to define an exit pathway 290 or lumen through end 294 of holder 217. Sleeve 293 is engaged to and mates with one end of microtubing 219. It is contemplated that spike 283 has a surface cut at an angle of about 30 degrees and is used to puncture a sealing diaphragm of anesthetic cartridge 221 when cartridge 221 is loaded into holder 217, as described below. It is contemplated that cartridge 221 is movable relative to spike 283 for aspiration using system 211.

Rear end 296 of cartridge holder 217 includes a pair of opposite radially projecting wings 273. Wings 273 engage and form an interference fit between end 296 and a receptacle 225 on housing 213. It is envisioned that receptacle 225 is formed along the top portion of housing 213, as shown in FIG. 7.

Receptacle 225 has a generally round opening 275 with a pair of oppositely disposed keyways 275A that are sized for receiving and accommodating wings 273 of cartridge holder 217. Receptacle 225 includes a pair of tongues 277 formed on each half 235, 237 of housing 233 below keyways 275A. A pair of corresponding cam members 279 are disposed above each tongue 277. Each set of corresponding tongues 277 and cam members 279 define a locking slot 278 there between.

Referring to FIG. 12, the forward end of holder 217 is provided with a plurality of holes 288. These holes can be used to assist in the removal of spent cartridges 221, as discussed below. Between these holes, there are provided a plurality of radial ribs 292A disposed inside holder 217 for stabilizing cartridge 221 after cartridge 221 is fully inserted into holder 217, in the position depicted in FIG. 13.

As shown in FIG. 13, anesthetic cartridge 221 includes a plastic or glass tube 291 defining an inside storage chamber containing a desired anesthetic. Tube 291 has a forward portion 292 and a rear portion 298. Forward portion 292 is formed with a neck region 289 and an extending mouth 288 in which a diaphragm 285 is adapted to be maintained in position within mouth 288 by a cap 287. Rear portion 298 has an end wall 285A, which acts as a piston to expel the anesthetic from cartridge 221, in conjunction with plunger 223.

To load anesthetic cartridge 221 into holder 217, forward portion 292 of cartridge 221 is inserted through rear end 296 until approximately a portion of cartridge 221 extends below end 296. Then, rear portion 298 and, more particularly, end wall 285A, is in contact with plunger 223, which selectively passes through receptacle 225 during operation. Once plunger 223 is properly aligned with cartridge 221, end 296 is seated within holder receptacle 225, as shown in FIG. 10, such that wings 273 are disposed within corresponding keyway 275.

To lock holder 217 within receptacle 225, end 296 is rotated one quarter turn in a counterclockwise direction (see FIG. 11) such that each of wings 273 passes through or snaps with a locking slot 278 and between corresponding tongue 277 and cam member 279. Plunger 223 is threadably by secured to a motor (not shown). Therefore, as receptacle 225 is secured in the counter-clockwise direction, plunger 223 is prevented from loosening. The distance between each tongue 277 and cam member 279 is slightly smaller than the thickness of wings 273. As each wing 273 turns through one of slots 278, respective tongue 277 flexes slightly downward. Once wing 273 passes through slot 278, tongue 277 snaps back, thereby locking the respective wing 273 in place. The rotation of holder 217 is terminated when wings 273 hit stops 278A.

It is envisioned that receptacle 225 with opening 275, keyways 275A, tongues 277, cam members 279 and stops 278A are formed within a domed portion 226 of top 236. The bottom of receptacle 225 is defined by transverse walls 310, 312. Walls 310, 312 have corresponding holes 314, 316 coaxial with opening 275, allowing piston 223 to reciprocate in and out of housing 213.

During the loading of anesthetic cartridge 221 into drive unit 211, cartridge 221 is urged forward toward end 294 such that spike 283 punctures diaphragm 285. This provides a pathway or lumen between inside chamber 222 and exit pathway 290 so that anesthetic may flow through microtubing 219 and to handpiece unit 215 (see FIG. 14). It is contemplated that holder 217 has an outer surface 218, which is not cylindrical but polygonal, as shown in FIG. 10. Surface 218 may have, for example, eight sides (octagonal in cross section). At rear end 296, surface 218 has plurality of axial ribs 220 extending forward, which facilitate engaging and disengaging holder 217 from housing 213. The octagonal shape of holder 217 facilitates the handling by the practitioner.

Referring to FIGS. 14-21, handpiece unit 215 includes a handle member 301 of a substantially elongated design and a needle assembly 303 selectively engaged to one end of handle member 301. Handle member 301 has a body 315 and a forward bulbous end or head 305, and a rear end 307. Forward end 305 is formed with an inwardly disposed luer thread 305A and an extending plug 309, both of which selectively engagable needle assembly 303.

Figure 16:
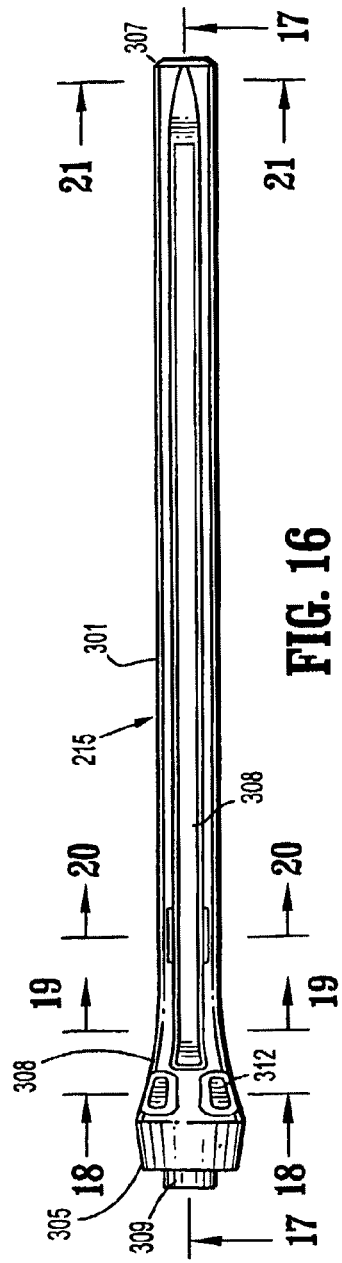
FIG. 16 is a side elevation view of a handle of the handpiece unit of the system shown in FIG. 7.
Figure 17:
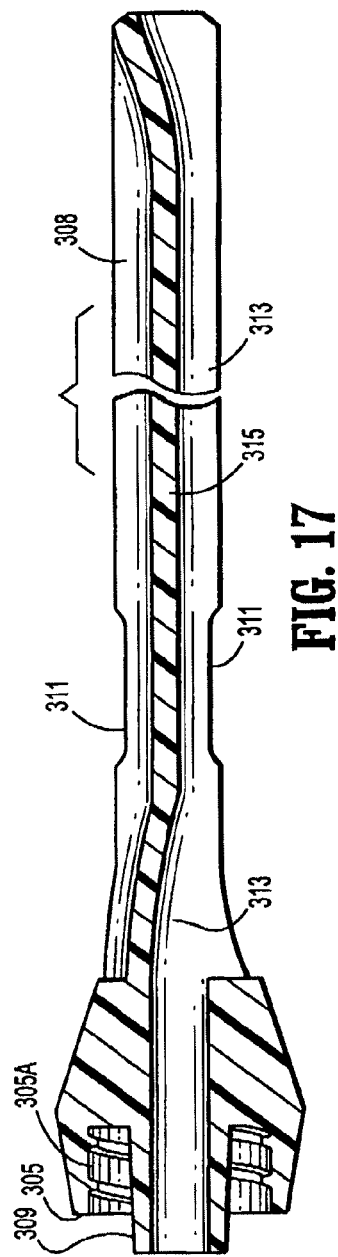
FIG. 17 is a side view in cross-section of the handle shown in FIG. 16.
Figure 21:
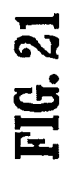
FIG. 21 is a cross-sectional view taken along line 21-21 of FIG. 16.
Figure 20:
FIG. 20 is a cross-sectional view taken along line 20-20 of FIG. 16.
Figure 19:
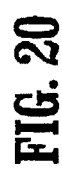
FIG. 19 is a cross-sectional view taken along line 19-19 of FIG. 16.
Figure 18:
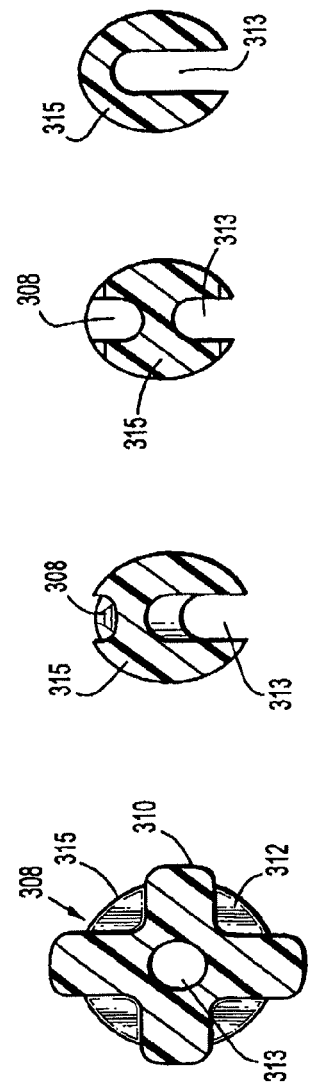
FIG. 18 is a cross-sectional view taken along line 18-18 of FIG. 16.

Body 315 defines a U-shaped elongated slot or trough 313 in which microtubing 219 is selectively seated starting at forward end 305 and ending at rear end 307 (see FIGS. 16 and 17). During assembly, one end of microtubing 219 is first threaded into plug 309 of end 305, after which, the rest of tubing 219 is press fit into slot 313. A solvent such as MEK (methylethyl ketone) may be used to permanently bond microtubing 219 in place.

Body 315 of handle member 301 further includes a longitudinal slot 308, which cooperates with pathway 313 to enhance the practitioner's ability to grasp handle member 301. Handle 301 is formed with a pair of cut-outs 311 adjacent forward end 305 to define a tapered weak zone in body 315. As a result, as shown in FIG. 14, handle 301 may be flexed and plastically deformed at the location of cut-outs 311 to properly orient needle assembly 303 during operation of system 211.

Figure 22:
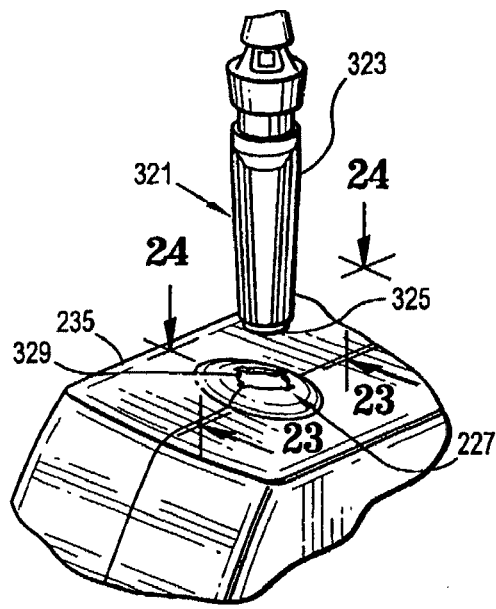
FIG. 22 is a perspective view illustrating one embodiment of the needle assembly for engagement with a storage receptacle of the system shown in FIG. 7.
Figure 23:
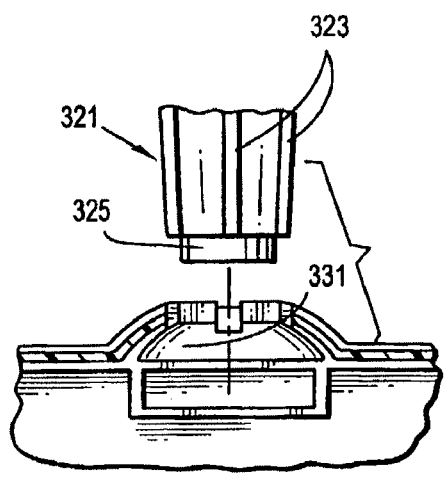
FIG. 23 is side elevation view, in partial cross-section, illustrating the engagement shown in FIG. 22.

As shown in FIGS. 15, 22 and 23, needle assembly 303 includes a needle cover 321 having a series of longitudinally extending ribs 323 formed along the outside surface thereof and a luer lock needle 302. Needle cover 321 has a forward end 325 configured for selective reception by handpiece receptacle 227 formed along top 236 of drive unit 213, and a rear end for selectively engaging with end 305 of handle member 301, thereby covering needle 302, which is permanently attached to sleeve 304 (FIG. 14). Sleeve 304 is in turn coupled to head 305 by the luer connection.

Figure 24:
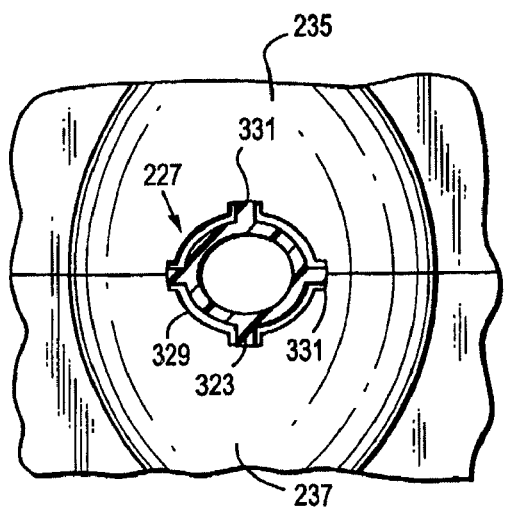
FIG. 24 is a top view, in partial cross-section, illustrating the engagement shown in FIG. 22.

Handpiece receptacle 227 of drive unit 211 is configured to hold needle cover 321 firmly in place for storage while handpiece 215 is in use such that cover 321 is removed from handle member 301. Handpiece receptacle 227 has an annular opening 329. Annular opening 329 has a circumference with four outwardly formed arcuate projections 331. To secure needle cover 321 in receptacle 227, cover 321 is placed in opening 329 such that ribs 323 are received within projections 331, as shown in FIG. 24.

In another alternate embodiment, in accordance with the present disclosure, a handpiece assembly 600 (FIG. 7) is provided that is adapted for use with a medication infusion system, such as, for example, dental anesthetic injection delivery system 211 described with regard to the FIGS. 7-24, which applies pressure to handpiece assembly 600 for delivering medication to a body. Handpiece assembly 600 includes a cartridge holder 217, which is configured for disposal of cartridge 221, microbore tubing 219, handpiece unit 215 and needle assembly 303. Cartridge holder 217 is connected with receptacle 225 of system 211 as described above. It is contemplated that dental anesthetic injection delivery system 211 is designed to apply pressure to handpiece assembly 600 in a specific pressure range, such as, for example, 200 psi to 650 psi, although other ranges are envisioned.

Tubing 219 is provided having a first end that is fixedly sealed with cartridge holder 217 such that cartridge holder 217 facilitates communication between tubing 219 and cartridge 221. Handpiece unit 215 is fixedly sealed with a needle 302 of needle assembly 303 and the second end of tubing 219 so that tubing 219 and needle 302 are in communication. It is envisioned that handpiece unit 215 can be bonded in a sealing configuration at a luer lock of needle 302 to handpiece unit 215 interface. This configuration advantageously avoids the requirement that the components of system 211 mesh with precise accuracy to create a barrier to leakage. Similarly, such a sealing configuration may be employed at the interface of tubing 219 and handpiece unit 215, and the interface of tubing 219 and cartridge holder 217. It is envisioned that needle assembly 303 includes a sleeve or needle hub.

The components of handpiece assembly 600 are fixedly or permanently sealed in a configuration that is impermeable to leakage. This advantageous configuration prevents leakage of medication or other gases, fluids, etc., outside of the sealed system 211 and assembly 600. It is envisioned that the components of handpiece assembly 600 may be sealingly bonded including a removable seal such that the components may be separated. It is contemplated that sealing and/or bonding of the components of handpiece assembly 600 can be achieved via various methodologies, such as, for example, adhesive, sonic bonding/welding, resin bonding agents, chemical bonding agents, etc. For example, a solvent such as MEK (methylethyl ketone) may be used to fixedly seal the components of handpiece assembly 600 in place.

It is envisioned that tubing 219 can be of varying lengths, such as, for example, 6 inches to 80 inches. It is further envisioned that tubing 219 is configured so that minimal distortion or deformation of shape occurs over a specific pressure range. For example, it is envisioned that tubing 219 will not deform or distort between 200 psi to 650 psi. Preferably, needle assembly 303 includes a 30 gauge ½ inch luer lock needle. It is, however, contemplated that other needle sizes and lengths may be used.

Handpiece assembly 600 is designed to facilitate operability of system 211, over a range of pressure for infusing medication safely and painlessly during a medical and/or dental procedure. Accordingly, handpiece assembly 600 includes a component that is configured to fail prior to the remaining components of handpiece assembly 600, thereby avoiding several known disadvantages such as, for example, leakage of anesthetic into patient tissues. This configuration also eliminates operator error in affixing needle 302 to handpiece unit 215. This configuration avoids medication or other gases, fluids, etc., from spraying out of a leakage point that can contaminate the practitioner or cause harm to the face, skin, nose or eyes. In this configuration, one of cartridge holder 217, tubing 219, needle assembly 303 or handpiece unit 215 is advantageously configured for a selective structural failure at a predetermined pressure threshold applied to handpiece assembly 600 from system 211.

It is contemplated that the structural failure may include physical deformation, dimensional changes, fracture, elongation, stretching or leakage. The predetermined pressure threshold may be in a range of 450 psi to 550 psi, although other ranges are envisioned. Alternatively, the predetermined pressure threshold can be a specific value, such as, for example, 525 psi, 550 psi, etc.

In one embodiment, cartridge holder 217 is configured for a selective structural failure, prior to tubing 219, handpiece unit 215 and needle assembly 303, at a predetermined pressure threshold, in the range of 450 to 550 psi, as applied to handpiece assembly 600 from system 211. Cartridge holder 217 is designed to physically deform to a sufficient degree to cause failure of cartridge holder 217, at a specific pressure range of 450 psi to 550 psi prior to failure of the remaining components of handpiece assembly 600. This configuration advantageously ensures that the other components of system 211 will not fail and result in leakage of medication into the patient's tissues. System 211 is designed with a predetermined weak point at cartridge holder 217 to ensure that failure results in breakage without leakage of medication.

In an alternate embodiment, wings 273 (FIGS. 8-13) of cartridge holder 217 can be configured for selective structural failure at the predetermined pressure threshold, such as by reduced wall thickness at the wing junction with cartridge holder 217. When the pressure in system 211 reaches the predetermined pressure threshold, wings 273 are caused to break and/or shear off. In this way, cartridge 221, microbore tubing 219, handpiece unit 215 and needle assembly 303 do not physically deform or fail. The practitioner is alerted to the failure and leakage of anesthetic does not occur. Thus, the disadvantages discussed above are avoided.

Figure 25:
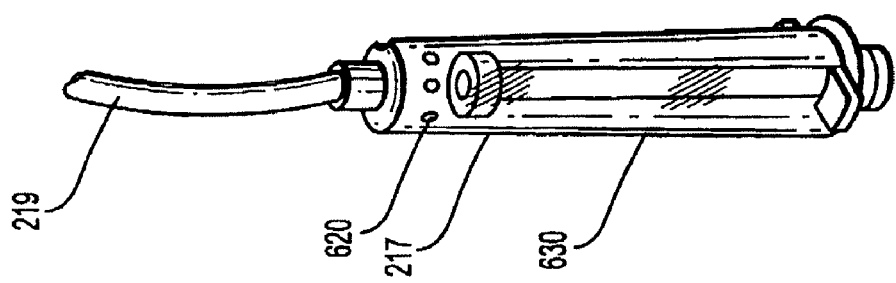
FIG. 25 is side perspective view of an alternate embodiment of a cartridge holder of the system shown in FIG. 7.

In an alternate embodiment, as shown in FIG. 25, cartridge holder 217 includes a plurality of lateral openings 620. Openings 620 facilitate selective structural failure of cartridge holder 217 at the predetermined pressure threshold. When the pressure in system 211 reaches the predetermined pressure threshold, openings 620 provide a weakness in sidewall 630 of cartridge holder 217, causing sidewall 630 to break and/or fracture. In this way, cartridge 221, microbore tubing 219, handpiece unit 215 and needle assembly 303 do not physically deform or fail. The practitioner is alerted to the failure and leakage of anesthetic does not occur. Thus, the disadvantages discussed above are avoided. Alternatively, the top of cartridge holder 217 has a plurality of openings 288 (FIG. 12). Openings 288 allow a weakening of the top wall of cartridge holder 217 so that failure will result in the separation of cartridge holder 217 at a point in which cartridge 221 stays embedded with spike 283, which penetrates a rubber diaphragm of cartridge 221.

Figure 26:
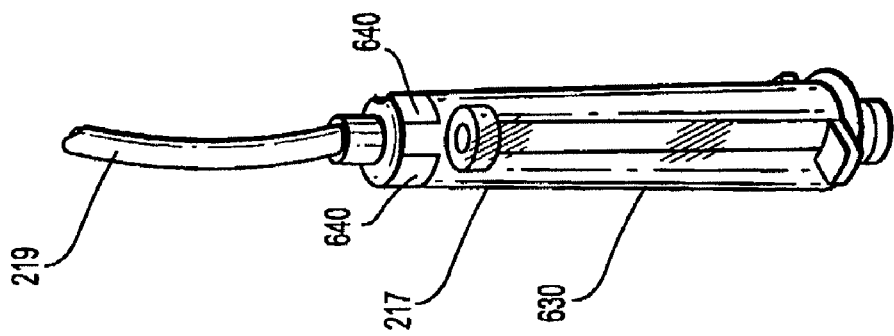
FIG. 26 is side perspective view of another alternate embodiment of a cartridge holder of the system shown in FIG. 7.

In an alternate embodiment, as shown in FIG. 26, cartridge holder 217 includes a plurality of lateral openings, such as, windows 640. Windows 640 facilitate selective structural failure of cartridge holder 217 at the predetermined pressure threshold. When the pressure in system 211 reaches the predetermined pressure threshold, windows 640 provide a weakness in the sidewall 630 of cartridge holder 217, causing sidewall 630 to break and/or fracture. In this way, cartridge 221, microbore tubing 219, handpiece unit 215 and needle assembly 303 do not physically deform or fail. The practitioner is alerted to the failure and leakage of anesthetic does not occur. Thus, the disadvantages discussed above are avoided. Alternatively, cartridge holder 217 may include a relatively thin-walled portion such that the thin-walled portion facilitates selective structural failure of cartridge holder 217 at the predetermined pressure threshold.

Cartridge holder 217 may also include spike 283 oriented to puncture cartridge 221 upon movement of cartridge 221 towards spike 283. System 211 can be configured to aspirate fluid from the body during movement of cartridge 221 away from spike 283. In an alternate embodiment, cartridge holder 217 is designed to facilitate the creation of a vacuum for bodily fluid/blood aspiration during use of system 211. For example, during the process of injecting drugs or fluids into bodily tissues, it may be advantageous to determine if the injection is being performed within specific tissues to avoid the direct placement of a medication into a blood vessel, e.g., artery or vein. The technique of creating a vacuum or an aspiration confirms the placement of needle 302 within a vessel. If blood or fluid is "sucked back" or aspirated into system 211, this confirms the placement of needle 302 within a vessel. It is contemplated that the practitioner may then reposition needle 302, if the intention was not disposal within a vessel. Cartridge holder 217 can also facilitate aspiration. Cartridge holder 217 includes spike 283 orientated to puncture a rubber diaphragm or the like of medication cartridge 221 upon placement of cartridge 221 within cartridge holder 217. Cartridge holder 217 is designed to be of a greater physical length relative to cartridge 221. This configuration facilitates movement of cartridge 221 relative to cartridge holder 217 and spike 283. As cartridge 221 is withdrawn from cartridge holder 217 and spike 283 by physical movement, a vacuum is created within cartridge 221. This vacuum created by the movement of cartridge 221, relative to cartridge holder 217 and spike 283 produces a vacuum or aspiration effect within handpiece assembly 600 during use.

Thus, system 211 can be configured to aspirate fluid from the body during movement of cartridge 221 away from spike 283. It is contemplated that cartridge holder 217 may contain the entire cartridge 221 during use. The action of withdrawing cartridge 221, whereby the relative movement of cartridge 221 to cartridge holder 217 along spike 283 produces the vacuum. In an alternate embodiment, it is envisioned that the principles of the present disclosure relating to handpiece assembly 600 may be adapted for use with other handpiece assemblies. See, for example, handpiece 20 disclosed in U.S. Pat. No. 6,428,517, the contents of which being hereby incorporated by reference herein.

In operation, system 211 is initialized when the power button is turned on. The practitioner then inserts cartridge 221 into cartridge holder 217 and positions the head of plunger 223 into the bottom of cartridge holder 217 so that this head abuts piston 285A. Cartridge holder 217 is then secured to housing 213 by pressing it down into receptacle 225 and twisting it clockwise by about 90 degrees, as discussed. This motion also forces cartridge holder 217 to slide over piston 223. This motion in turn causes spike 283 to move downward and break seal 292, thereby opening cartridge 221. Thus, in one movement, cartridge holder 217 is mounted onto housing 213 and, at the same time, cartridge 221 is unsealed. A practitioner may employ system 211 for a desired infusion and/or aspiration application, such as, for example, medical and dental applications using the methods disclosed herein. For example, in a periodontal ligament ("PDL") injection application, the practitioner places needle 302 within a specific anatomic space that cannot be directly visualized as it is being performed. Needle 302 is positioned within a small space that is found between the root of a tooth of a patient (not shown) and the supporting bone that holds the tooth within the jaw bone. This space is typically 0.25 millimeter (mm) in distance, between the tooth and the bone. This anatomic location is composed of a ligament that connects the tooth to the bone, which is the periodontal ligament. The PDL is typically 3 to 5 mm below the edge of the gum (free gingival margin) and therefore it is not readily visible when trying to find this location.

The PDL is composed of high resistance tissues. The PDL becomes a pathway to allow the anesthetic solution to pass through and reach the final target for the anesthetic solution, which is the nerves that enter a tooth. An effective means of optimizing the rate of flow to the bottom of the tooth is by controlling the pressure during this process. Continual adjustments to maintain an effective pressure gradient promotes optimal fluid transfer. Too much pressure within the tissues, i.e., excessive high-pressure above 650 psi, as found with a traditional or manual syringe, can cause fluid over pressurization and damage. In cases of undesirably low pressure (below 200 psi), the fluid will not overcome tissue resistance needed to produce adequate fluid flow through the PDL tissues, producing an ineffective outcome. Therefore, pressure and flow-rate are considered factors in all injections, particularly, the PDL injection. In the PDL injection, both of these parameters can be controlled with the presently disclosed systems, such as, for example, system 211, to ensure a safe and effective outcome.

An optimum range of 200 psi to 650 psi can be maintained for the PDL injection. Maintaining optimum fluid parameters of pressure and flow-rate for the PDL injection help promote effective fluid flow, allowing a greater volume of solution to reach the target site while minimizing tissue damage to the periodontal tissues. System 211 maintains pressure at a specified flow-rate, for example, 0.005 milliliters per second (ml/sec) and may vary depending on differing conditions desired or encountered. In the PDL injection, this method maintains reduced pressure, promoting larger drug volume delivery while minimizing pain and the risk of tissue damage.

In addition, needle 302 enters this location and maintains integrity with the location during the entire injection. As needle 302 enters into the PDL, it creates a seal so that the anesthetic solution will flow through the PDL and into the bone. Eventually, the anesthetic solution reaches the bottom of the tooth to deposit solution at the nerves prior to entering into the tooth. If the seal of needle 302 cannot be maintained, leakage of the anesthetic solution will occur into the patient's mouth, which will result in failure of the desired effect of anesthetizing the nerve of the tooth.

The system described herein advantageously prevents failure of the desired effect. System 211 provides the practitioner with information relating to the proper position of needle 302, discussed above, within the PDL via data visually sensed or audibly heard from measuring exit pressure and/or measuring pressure within system 211 used to perform the PDL injection. This real-time monitoring of pressure ensures that the practitioner has located the correct anatomical PDL location. The pressures measured within the PDL location have been found to be between 200 psi to 650 psi when a rate of administration is at 0.005 ml/sec. It is contemplated that the use of a different rate of administration is anticipated to produce a different range of pressure produced to properly locate the PDL for a given patient. In addition, the range discussed herein, 200 psi to 650 psi, represents a range that is reflective of the anatomical variations commonly found between different patients. Other ranges are contemplated.

It is further contemplated that these variations may be influenced by the patient's age, gender, bone density, and a multitude of normally occurring anatomic variations found between patients. The pressure range defined allows the practitioner to determine if needle 302 is outside of the correct location. For example, the pressure may drop below 200 psi, informing the practitioner that leakage of the anesthetic solution is occurring within the patient's mouth and will not be successful. Alternatively, the pressure may rise above 650 psi, which indicates that needle 302 may be occluded or blocked from proper flow. Pressures exceeding 650 psi alert the practitioner that the injection will not be successful or damage may occur to the patient tissues from excessive pressures. The pressure range defined and described enables the practitioner to identify the PDL, which is not directly visualized during location of the PDL itself. Hence, the practitioner relies on the pressure data collected in real-time to determine the position of needle 302 with the correct anatomic location. The pressure range described allows a larger volume of anesthetic solution to be delivered, such as, for example, volumes above 0.9 ml to be administered.

Thus, the advantageous systems and methods described facilitate a PDL injection that utilizes the fluid pressure to identify and determine the PDL location to achieve the desired outcome.

System 211 under microprocessor control, delivers precise pressure and volume ratios of anesthetic. Even in resilient dental tissue, such as the palate and periodontal ligament, system 211 delivers an anesthetic drip that precedes needle entry, effectively creating an anesthetic pathway. This combination of an anesthetic pathway and controlled flow rate results in a virtually imperceptible injection and rapid onset of profound anesthesia, all for the patient's comfort and relief. In addition, system 211 affords greater tactile control than traditional dental syringe units, and precise needle placement is therefore facilitated.

Figure 27:
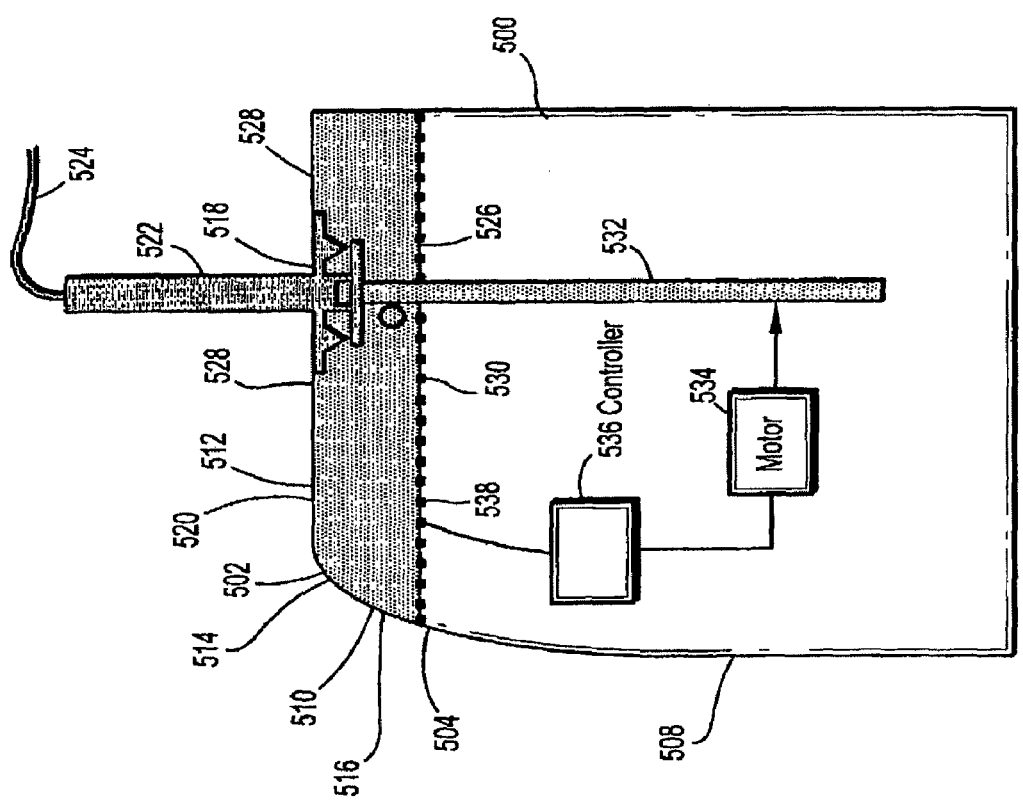
FIG. 27 is a side view of an alternate embodiment of the system shown in FIG. 7.

In another alternate embodiment, a sensor module can be added on top of the housing of system 20, similar to that described. Referring to FIG. 27, a housing 500 has a top surface 502 and a front surface 504. Disposed on front surface 504 are a plurality of indication lights and control buttons 508. A sensor module 510 is mounted on top surface 502. Module 510 includes an upper surface 512 and a front surface 514, which has an LCD display 516.

Top surface 512 has a receptacle 518 and a hole 520. Attached to module 510 is a cartridge 522 connected to the proximal end of a tubing 524. The distal end of tubing 524 is connected to a syringe, a catheter or other similar injection device (not shown). When not in use, this injection device can be stored in hole 520. Bottom 526 of cartridge holder 522 is shaped so that it can be inserted quickly and easily into receptacle 518 and form an interference fit therewith. It is contemplated that a quick-connect coupling is provided between bottom 526 and receptacle 518 so that cartridge holder 522 can be quickly and easily installed onto and removed from receptacle 518. Cartridge holder 522 holds a cartridge with an anesthetic or other medicinal substance (not shown). One or more sensors 528 are positioned between bottom 526 and the walls of receptacle 518. These sensors may be pressure sensors or other similar sensors used to monitor the force applied to the liquid being expelled through tubing 524.

Module 512 holds a plunger sensor 530 that is disposed in close proximity to, or in contact with plunger 532. As plunger 532 moves upward, its tip enters into the cartridge in cartridge holder 532 and forces its contents to be expelled through tubing 524. Moving plunger 532 downwardly causes aspiration. Plunger sensor 530 measures the direction and, optionally, the rate of movement of plunger 532.

Plunger 332 is reciprocated vertically by a motor 534. Motor 534 is controlled by a controller 536. Sensors 528 and 530 are coupled to an interface 538. Interface 538 transmits information from sensors 528, 530 to controller 536. Controller 536 then operates motor 534 to cause plunger 532 in the same manner, and using the same algorithm as plunger 94 described with regard to FIGS. 1-4. The information associated with this operation, and other information are displayed on display 516.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A medication infusion system comprising:
    a drive unit having a receptacle and being configured to apply pressure in a range of 200 psi to 650 psi, to a hand piece assembly for delivering medication to a body;
    a disposable handpiece assembly detachably connected to the drive unit, the handpiece assembly comprising:
        a cartridge holder being configured for disposal of a medication cartridge, the cartridge holder having an end for receiving a medication cartridge, the end of the cartridge holder having a plurality of wings and being connected with the receptacle of the medication infusion system by an interference fit of the wings inside the receptacle;
        microbore tubing having a first end and a second end, the first end being fixedly sealed by bonding that is impermeable to leakage with the cartridge holder such that the cartridge holder facilitates communication between the tubing and the medication cartridge;
        a needle assembly with a needle for injecting a patient's tissue;
        a handpiece being fixedly sealed by bonding that is impermeable to leakage with the needle assembly and by bonding that is impermeable to leakage with the second end of the tubing such that the tubing and the needle assembly are in communication;
        the wings of the cartridge holder being connected to the end of the cartridge holder at wing junctions that have a reduced wall thickness configured for structural failure, such that the wing junctions break at a predetermined threshold in the range of 450 to 550 psi, as applied to the handpiece assembly from the medication infusion system, such that the interference fit between the wings and the receptacle fails at the predetermined pressure threshold and thereby disconnects the cartridge holder from the drive unit so that the drive unit can no longer apply any pressure to the handpiece assembly.

2. A medication infusion system as recited in claim 1, wherein the needle includes a needle sleeve configured to seal with the handpiece.

3. A medication infusion system as recited in claim 1, wherein the predetermined pressure threshold is 550 psi.

4. A medication infusion system as recited in claim 1, wherein the cartridge holder includes at least two radially projecting wings configured for engagement with the receptacle of the medication infusion system.

5. A medication infusion system as recited in claim 1, including a cartridge received in the cartridge holder and wherein the cartridge holder includes a spike oriented to puncture the cartridge, the cartridge being configured for movement relative to the cartridge holder and the spike.

6. A medication infusion system as recited in claim 5, wherein the medication infusion system is configured to aspirate fluid from the body during movement of the cartridge away from the spike.

7. A medication infusion system as recited in claim 1, wherein the cartridge holder includes lateral openings that define windows in sidewalls of the cartridge holder.

8. A medication infusion system as recited in claim 1, wherein the tubing resists shape deformation in the applied pressure range between 200 psi to 650 psi.

9. A medication infusion system comprising:
   a drive unit having a receptacle and being configured to apply pressure in a range of 200 psi to 650 psi, to a hand piece assembly for delivering medication to a body;
   a disposable handpiece assembly detachably connected to the drive unit, the handpiece comprising:
      a cartridge holder being configured for disposal of a medication cartridge, the cartridge holder having an end for receiving a medication cartridge, the end of the cartridge holder having a plurality of wings and being connected with the receptacle of the medication infusion system by an interference fit of the wings inside the receptacle;
      microbore tubing having a first end and a second end, the first end being fixedly sealed by bonding that is impermeable to leakage with the cartridge holder such that the cartridge holder facilitates communication between the tubing and the medication cartridge;
      a needle assembly with a needle for injecting a patient's tissue;
      a handpiece being fixedly sealed by bonding that is impermeable to leakage with the needle assembly and by bonding that is impermeable to leakage with the second end of the tubing such that the tubing and the needle assembly are in communication;
      the wings of the cartridge holder being connected to the end of the cartridge holder at wing junctions that have a reduced wall thickness configured for structural failure, such that the wing junctions break at a predetermined threshold in the range of 450 to 550 psi, as applied to the handpiece assembly from the medication infusion system, such that the interference fit between the wings and the receptacle fails at the predetermined pressure threshold and thereby disconnects the cartridge holder from the drive unit so that the drive unit can no longer apply any pressure to the handpiece assembly;
   the medication infusion system further comprising:
   a sensor coupled to the drive unit for sensing an internal parameter indicative of the pressure being applied by the drive unit and internal resistances within the medication infusion system; and
   a controller coupled to the sensor and the drive unit, the controller including a calculator for calculating an exit pressure of the medication at the needle assembly, the controller generating commands to ensure the exit pressure does not exceed a predetermined level.

10. A medication infusion system as recited in claim 9, wherein the needle includes a needle sleeve configured to seal with the handpiece.

11. A medication infusion system as recited in claim 9, wherein the predetermined pressure threshold is 550 psi.

12. A medication infusion system as recited in claim 9, wherein the cartridge holder includes at least two radially projecting wings configured for engagement with the receptacle of the medication infusion system.

13. A medication infusion system as recited in claim 9, including a cartridge received in the cartridge holder and wherein the cartridge holder includes a spike oriented to puncture the cartridge, the cartridge being configured for movement relative to the cartridge holder and the spike.

14. A medication infusion system as recited in claim 13, wherein the medication infusion system is configured to aspirate fluid from the body during movement of the cartridge away from the spike.

15. A medication infusion system as recited in claim 9, wherein the cartridge holder includes lateral openings that define windows in sidewalls of the cartridge holder.

16. A medication infusion system as recited in claim 9, wherein the tubing resists shape deformation in the applied pressure range between 200 psi to 650 psi.

* * * * *